United States Patent
Minato et al.

(10) Patent No.: US 7,918,838 B2
(45) Date of Patent: Apr. 5, 2011

(54) DISPOSABLE DIAPER

(75) Inventors: Hironao Minato, Kagawa-ken (JP);
Kaiyo Nakajima, Kagawa-ken (JP);
Naoko Takada, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 505 days.

(21) Appl. No.: 11/849,666

(22) Filed: Sep. 4, 2007

(65) Prior Publication Data

US 2008/0065036 A1 Mar. 13, 2008

(30) Foreign Application Priority Data

Sep. 8, 2006 (JP) ................................. 2006-244551

(51) Int. Cl.
*A61F 13/15* (2006.01)
(52) U.S. Cl. ....... 604/385.09; 604/385.101; 604/385.19; 604/385.22
(58) Field of Classification Search ............. 604/385.09, 604/385.101, 385.19, 385.22
See application file for complete search history.

(56) References Cited

U.S. PATENT DOCUMENTS

| | | | | |
|---|---|---|---|---|
| 3,532,093 A * | 10/1970 | Lovret | ........................... | 604/348 |
| 3,995,640 A * | 12/1976 | Schaar | ........................... | 604/389 |
| 4,886,511 A * | 12/1989 | Korpman | ........................ | 604/365 |
| 5,269,775 A * | 12/1993 | Freeland et al. | ......... | 604/385.22 |
| 5,601,544 A * | 2/1997 | Glaug et al. | ............. | 604/385.28 |
| 6,183,458 B1* | 2/2001 | Ahlstrand et al. | ........ | 604/385.19 |
| 6,464,678 B2* | 10/2002 | Shimoe et al. | ........... | 604/385.27 |
| 6,508,798 B1 | 1/2003 | Widlund et al. | | |
| 6,632,974 B1 | 10/2003 | Suzuki et al. | | |
| 6,692,475 B2* | 2/2004 | Mishima | ................. | 604/385.19 |
| 2004/0039363 A1* | 2/2004 | Sugiyama et al. | ..... | 604/385.101 |

FOREIGN PATENT DOCUMENTS

| | | |
|---|---|---|
| JP | 61-41304 A | 2/1986 |
| JP | 01-285265 A | 11/1989 |
| JP | 2002-011044 A | 1/2002 |
| JP | 2002-301097 A | 10/2002 |

* cited by examiner

*Primary Examiner* — Loan Thanh
*Assistant Examiner* — Lynne Anderson
(74) *Attorney, Agent, or Firm* — Lowe, Hauptman, Ham & Berner, LLP (57) ABSTRACT

A disposable diaper including, a covering chassis having front and rear waist regions, and a crotch region; a body fluid absorbent structure disposed at least in the crotch region; and an elastic isolating sheet covering at least the absorbent structure. The elastic isolating sheet has a front opening and a rear opening. The absorbent structure is provided on a bottom thereof with an elastic panel.

17 Claims, 11 Drawing Sheets

DISPOSABLE DIAPER

The present application is based on, and claims priority from, Japanese Patent Application No. 2006-244551 filed on Sep. 8, 2006, the disclosure of which is hereby incorporated by reference herein in its entirety.

BACKGROUND OF THE INVENTION

The present invention relates generally to a disposable diaper.

It is known disposable diapers provided with an isolating sheet interposed between an absorbent assembly and a wearer's skin in order to protect the wearer's skin from being soiled with body waste. Such diapers are disclosed, for example, in Japanese Unexamined Patent Application Publication No. 1986-41304 (Reference 1) and Japanese Unexamined Patent Application Publication No. 2002-11044 (Reference 2).

In the case of the disposable diaper disclosed in Reference 1, a hydrophobic topsheet is provided above a cover sheet in an absorbent batt structure. This topsheet has an opening adapted to receive body waste such as feces and elastic bands extending on both sides of an opening in a back-and-forth direction of the diaper so as to be extendible in this direction. Upon putting this diaper on the wearer, the elastic bands contract and thereby the topsheet is spaced apart upward from the absorbent pad into contact with the wearer's skin so as to prevent the absorbent pad from coming in contact with the wearer's skin.

The diaper disclosed in Reference 2 is of pants-type and includes a skin contact sheet above a liquid-pervious topsheet used to cover an absorbent core. This skin contact sheet has, in a crotch region, an opening adapted to receive feces and elastic members extending between a front waist region and a rear waist region are attached in stretched states to the skin contact sheet so as to surround the opening.

In the case of the diaper disclosed in Reference 1, an absorbent region in a crotch region may be formed with a plurality of gathers extending in the back-and-forth direction and/or folded in two in a width direction of the diaper as the wearer closes his or her legs. Consequentially, it may be made difficult for feces to pass through the opening. If the absorbent panel is formed with gathers or folded in two, the effective area to come in contact with feces may be apparently decreased and absorption of the liquid constituent of feces may be retarded.

In the case of the diaper disclosed in Reference 2, the opening of the skin contact sheet may be rarely closed but an absorbent panel underlying the opening may be formed with gathers and/or folded in two as the wearer closes his or her legs. Consequentially, it may be made substantially difficult for feces to pass through the opening and/or absorption of the liquid constituent of feces by the absorbent panel may be retarded.

SUMMARY OF THE INVENTION

In view of the problems as have been described above, it is an object of the invention to improve the known diaper of prior art as has exemplarily described above so that an adequately large space to receive feces can be easily and reliably formed between the absorbent panel and the isolating sheet disposed thereon.

In accordance with the present invention, there is provided an improvement for a disposable diaper having a back-and-forth direction and a width direction, a bodyside and a non-bodyside opposed to the bodyside, the diaper comprising: a covering chassis having a front waist region, a rear waist region and a crotch region therebetween; an absorbent structure disposed on the bodyside of at least the crotch region; an elastic isolating sheet covering at least the absorbent structure and having front and rear end portions and an intermediate portion therebetween, front and rear openings for receiving body waste partitioned by the intermediate portion, and at least the intermediate portion being adapted to be spaced apart from the absorbent structure under contraction of the elastic isolating sheet, thereby preventing the absorbent structure and a wearer's skin from coming in contact with each other.

The improvement according to the present invention is in that an elastic panel is attached to the non-bodyside in a zone of the absorbent structure in the crotch region.

According to a preferred embodiment of the invention, the elastic panel is adapted to exert a higher rate of elastic restoration than that of any non-elastic constituent material of the diaper in the crotch region when the elastic panels bows at least in one of the back-and-forth direction and the width direction.

According to another embodiment of the invention, the absorbent structure comprises an absorbent panel including a liquid-pervious first sheet located on the bodyside, and a liquid-absorbent core covered with a liquid-impervious second sheet located on the non-bodyside.

According to another embodiment of the invention, the elastic panel has a width corresponding to 20 to 100% of the width of the absorbent core in a bottom of the crotch region.

According to further preferred embodiment of the invention, the absorbent core is thin and flexible particularly in its region overlapped the elastic panel.

According to further preferred embodiment of the invention, the absorbent core is thin and flexible particularly in its region overlapping the elastic panel.

According to yet further another preferred embodiment of the invention, the absorbent core is formed in its region overlapping the elastic panel with an opening extending through the absorbent core in a thickness direction thereof.

According to still further yet another preferred embodiment of the invention, string-like elastic members attached to the absorbent core ahead of the elastic panel so as to extend across the absorbent core.

According to still yet a further preferred embodiment of the invention, the elastic panel is attached to a bottom surface of the absorbent panel.

According to still yet a further preferred embodiment of the invention, the elastic panel is made of a material selected from the group consisting of foamed polyurethane, foamed polyethylene, foamed polystyrene, crimped thermoplastic synthetic fibers and hollow thermoplastic synthetic fibers.

According to still another alternative preferred embodiment of the invention, a bottom surface of the absorbent panel is formed of a laminate composed of a liquid-impervious plastic film and a nonwoven fabric or a plastic film respectively covering both surfaces of the plastic film.

With the disposable diaper according to the present invention, upon putting it on the wearer, the elastic isolating sheet contracts in the back-and-forth direction and consequently at least the intermediate portion of the elastic isolating sheet is spaced apart from the absorbent structure so as to come in contact with the wearer's skin. At the same time, the elastic panel provided in the crotch region functions to prevent a non-elastic constituent material of the diaper, particularly, the absorbent panel, particularly the core located in the crotch region being folded in two and/or formed with a plurality of gathers and thereby to ensure adequately large space between the elastic isolating sheet and the absorbent panel when the wearer closes his or her legs. Even if the absorbent panel is temporarily folded in two, the absorbent panel easily restores its initial state and quickly recovers the large space between the isolating member and the absorbent panel as soon as the wearer opens his or her legs.

According to the embodiment of the invention, wherein the elastic panel is located to a bottom of the absorbent structure, the foregoing effect due to the elastic panel mentioned above is much heightened.

According to the embodiment of the invention wherein the absorbent panel is thin and flexible particularly in its region overlapping the elastic panel and the absorbent panel is formed in this region overlapping the elastic panel with an opening extending through the absorbent core in a thickness direction thereof, it is unlikely that the elastically restorative force of the elastic panel might be diminished by the absorbent core even if the elastic panel is deformed. Consequentially, the space between the elastic panel and the inner sheet can be easily and reliably maintained.

According to the embodiment of the invention wherein string-like elastic members attached to the outer surface of the absorbent core ahead of the elastic panel so as to extend across the absorbent core, it is substantially prevented that the front portion of the crotch region might be folded in two in the width direction and, even if the front portion of the crotch region is folded in two, the front portion can easily restore the initial state.

Effects of the invention to be achieved in the other embodiments will be more fully understood from the detailed description given hereunder.

DETAILED DESCRIPTION OF THE PREFERRED EMBODIMENTS

The disposable diaper according to the present invention will be more fully understood from the description given hereunder with reference to the accompanying drawings.

Figure 1:
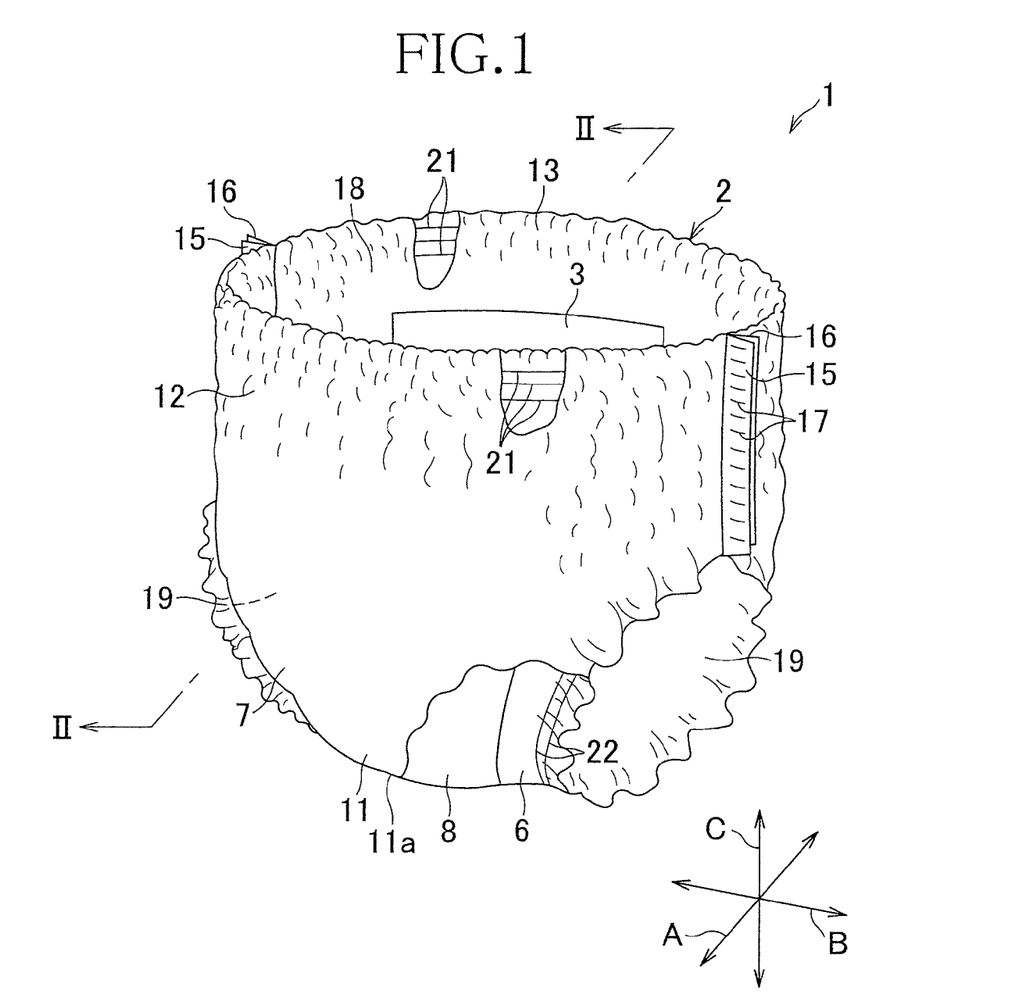
FIG. 1 is a partially cutaway perspective view of a diaper.
Figure 2:
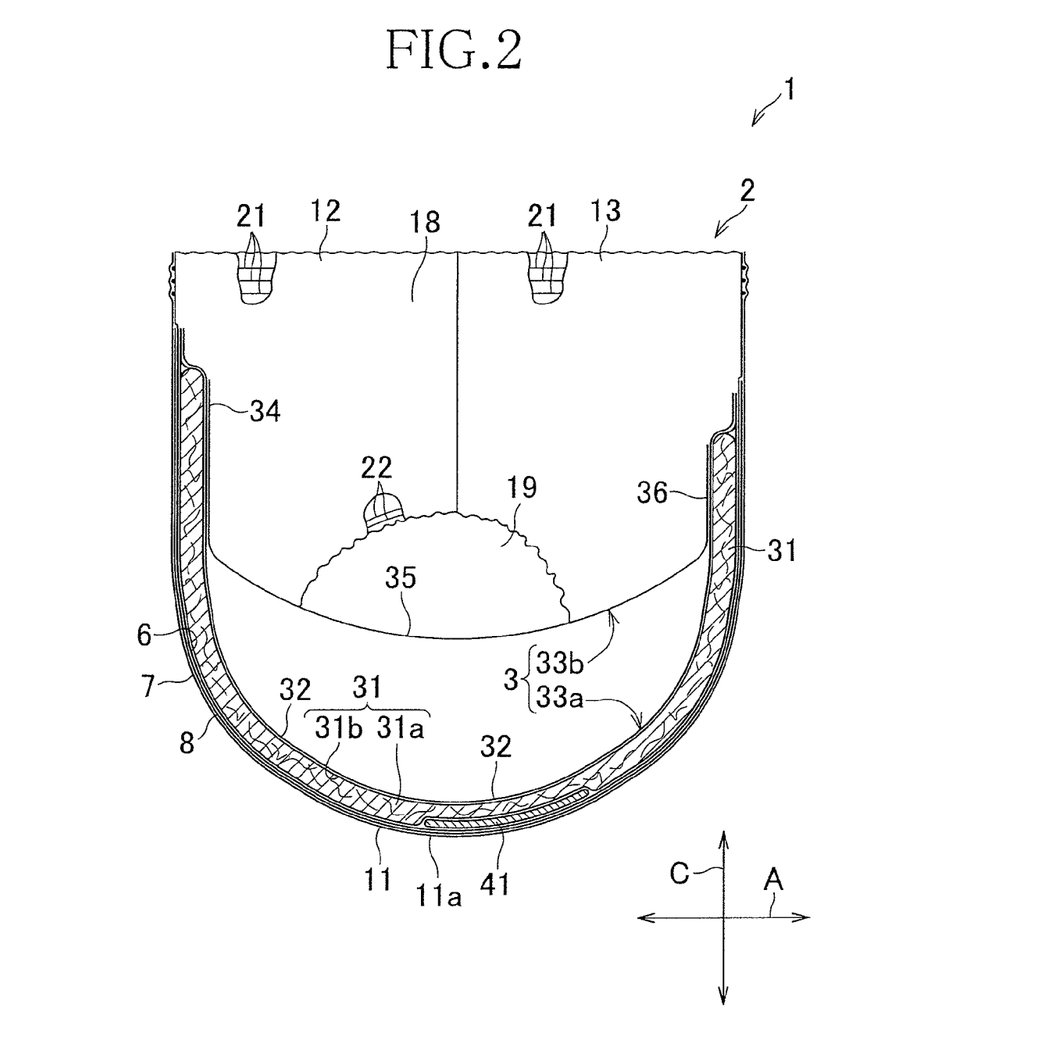
FIG. 2 is a sectional view taken along the line II-II in FIG. 1.

FIG. 1 is a partially cutaway perspective view of a diaper 1 and FIG. 2 is a sectional view taken along the line II-II in this perspective view. The diaper 1 is shown in FIG. 1 as put on the wearer and has a back-and-forth direction A, a transverse direction B and a height direction C and a bodyside I and a non-bodyside O opposed to the bodyside. The diaper 1 comprises a covering chassis 2 and a body fluid absorbent structure 3 provided on the bodyside I of the covering chassis 2. The covering chassis 2, in turn, comprises an inner sheet 6, an outer sheet 7 and a liquid-impervious sheet 8 sandwiched between these two sheets 6, 7 so as to define a front waist region 12, a rear waist region 13 and a crotch region 11 extending between these regions 12, 13. The front and rear waist regions 12, 13 respectively have opposed lateral margins 15, 16 overlapped with each other and joined together at a plurality of spots 17 arranged intermittently in the height direction C as viewed in FIG. 1 so as to form a waist-opening 18 and, at the same time, the front and rear waist regions 12, 13 cooperate with the crotch region 11 to form a pair of leg-openings 19. Along respective peripheral edges of the waist-opening 18 and the leg-openings 19, a plurality of waist elastic members 21 and leg elastic members 22 are laid between the inner sheet 6 and the outer sheet 7 and bonded at a stretched state to at least one of these sheets 6, 7. The absorbent structure 3 is provided at least in the crotch region 11 and comprises a liquid-absorbent panel 33a and an elastic isolating sheet 33b. The absorbent panel 33a comprises, in turn, a body fluid absorbent core 31 formed of a liquid-absorbent material 31a wrapped with a tissue paper 31b and a liquid-pervious inner sheet 32 covering at least a partial surface of the core 31 facing the wearer's skin. The elastic isolating sheet 33b is provided on the bodyside the inner sheet 32. Referring to FIG. 2, the elastic isolating sheet 33b has a front end portion 34 and a rear end portion 36 bonded to at least the inner sheet 32 at least in the front and rear waist regions 12, 13, respectively and an intermediate portion 35 spaceable apart upward from the inner sheet 32 in the crotch region 11. Referring again to FIG. 2, the core 31 is sandwiched between the inner sheet 32 and the leak-barrier sheet 8 so as to be covered with the leak-barrier sheet 8 from the outer side of the diaper 1. With this arrangement, it is unlikely that body fluid once absorbed by the core 31 might leak from the diaper 1. Between the absorbent panel 33a and the inner sheet 6, there is provided an elastic panel 41.

Figure 3:
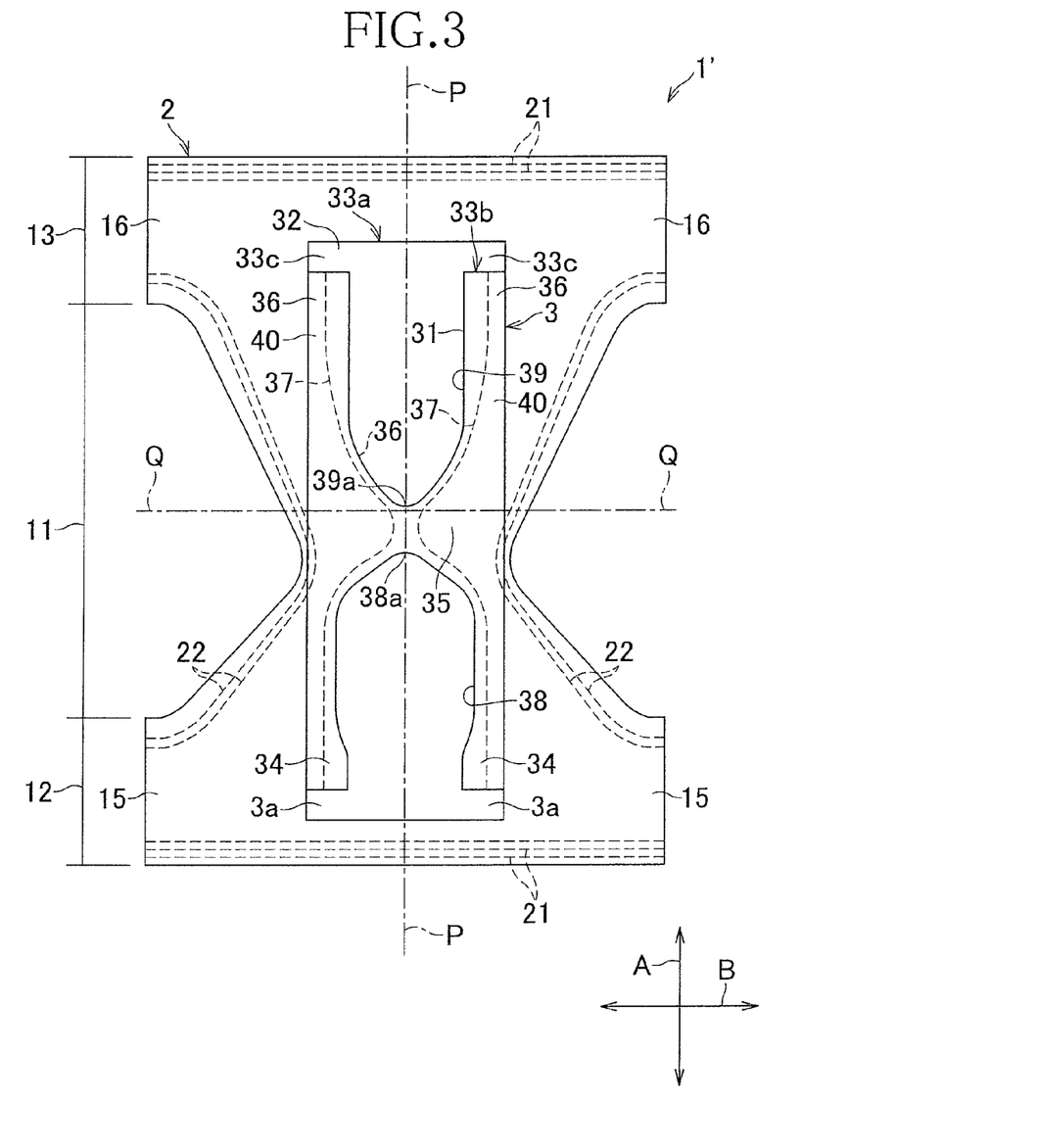
FIG. 3 is a developed view of the diaper of FIG. 1.

FIG. 3 is a plan view showing the diaper 1' corresponding to the diaper 1 of FIG. 1 with the front and rear waist regions 12, 13 having been forcibly peeled off from each other at the spots 17 and developed in the back-and-forth direction A. In FIG. 3, waist elastic members 21, leg elastic members 22, and crotch elastic members 37 attached in stretched states to the elastic isolating sheet 33b are indicated by chained lines. The diaper 1' has a longitudinal center line P-P bisecting a width of the diaper 1' and a transverse center line Q-Q bisecting a length of the diaper 1' in the back-and-forth direction A wherein the diaper 1' is configured to be symmetric about the center line P-P. The covering chassis 2 is generally hourglass-shaped and the absorbent structure 3 is rectangular. The elastic isolating sheet 33b provided in association with the absorbent structure 3 comprises lateral portions 40 extending along lateral edges 3a of the absorbent panel 33a and the intermediate portion 35 connecting the lateral portions 40 which are elasticized by the crotch elastic members 37. The lateral portions 40 cooperate with the intermediate portion 35 to define a generally U-shaped front opening 38 put aside toward the front waist region 12 and a U-shaped rear opening 39 put aside toward the rear waist region 13. The diaper 1 is adjustably put on the wearer so that the wearer's external genital lies in the front opening 38, the wearer's anus lies in the rear opening 39 and, between the external genital and the anus, at least the intermediate portion 35 comes in contact with the wearer's skin. In this state, it is preferable that a closed portion 38a of the U-shape generally defined by the front opening 38 is located in front of the transverse center line Q-Q while a closed portion 39a of the U-shape generally defined by the rear opening 39 is located in a vicinity of the transverse center line Q-Q. The crotch elastic members 37 in stretched states contract in the back-and-forth direction A as the crotch region 11 bows in the back-and-forth direction A as seen FIGS. 1 and 2. Consequentially, the crotch elastic members 37 function to reduce the dimension of the elastic isolating sheet 33b as viewed in FIG. 3 and simultaneously to space apart upward the intermediate portion 35 from the inner sheet 32 (See FIG. 2).

Figure 4:
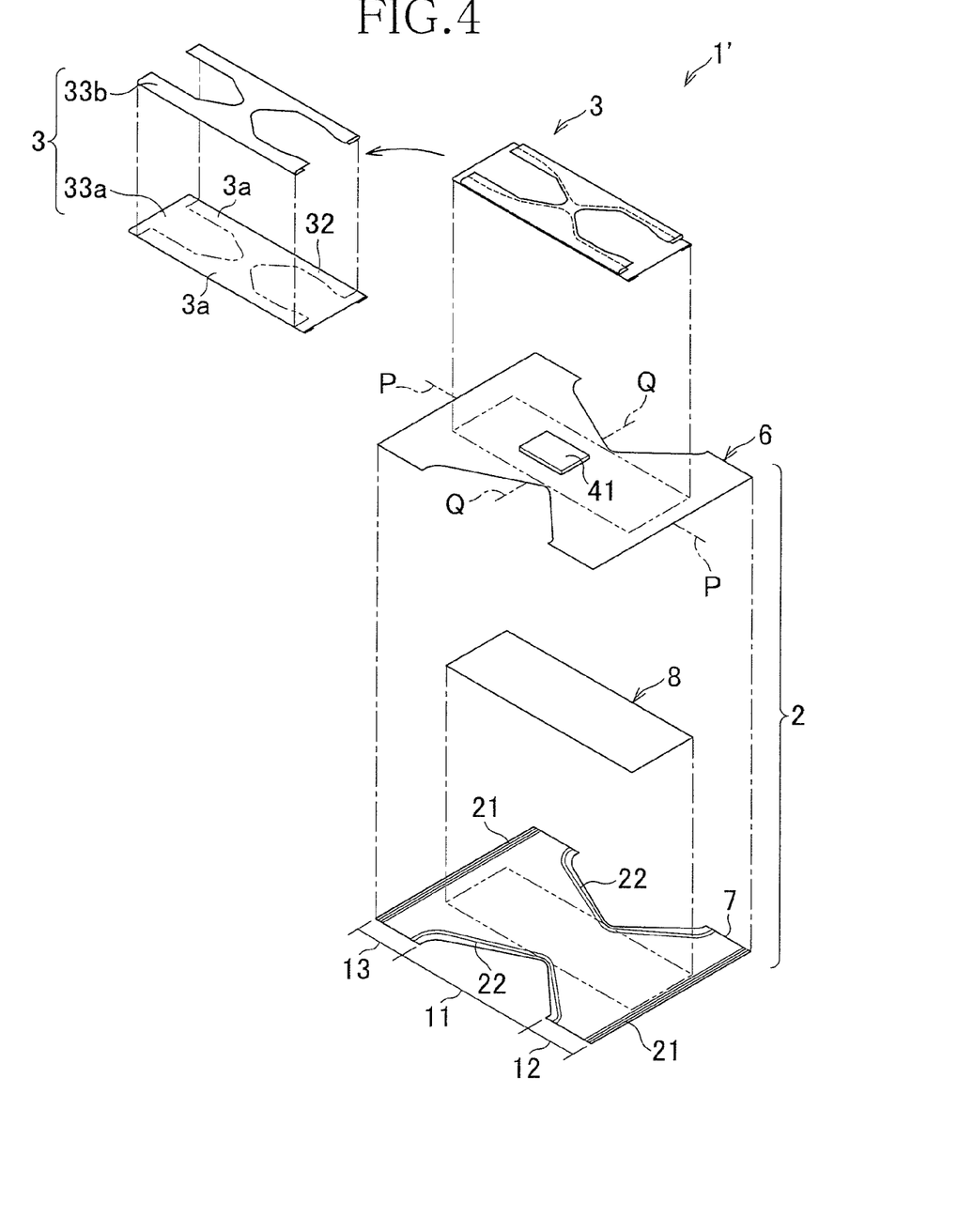
FIG. 4 is an exploded assembly diagram of the diaper of FIG. 3.

FIG. 4 is an exploded view illustrating structure of the diaper 1'. The outer sheet 7 is formed of a nonwoven fabric or plastic film and provided on the inner surface thereof with the waist elastic members 21 and the leg members 22 attached in stretched states thereto by means of hot melt adhesives (not shown). The outer sheet 7 is further provided on the inner surface thereof with the leak-barrier sheet 8 attached thereto by use of adhesives or any suitable sealing techniques. The outer sheet 7 and the leak-barrier sheet 8 are provided, in turn, on the respective inner surfaces with the inner sheet 6 of a nonwoven fabric or plastic film which is the same as the outer sheet 7 in shape as well as in size attached thereto by use of adhesives or any suitable sealing techniques. The inner sheet 6 is provided on the inner surface thereof with an elastic panel 41 attached thereto by means of hot melt adhesives (not shown) so as to be located symmetrically about the longitudinal center line P-P. In the case of the diaper 1 when it is designed as baby diapers, the elastic panel 41 is preferably dimensioned to have a width corresponding to 20 to 100% of the width of the core 31 as measured at a bottom 11a of the crotch region 11 (See FIGS. 1 and 2) lying on the transverse center line Q-Q and a length of 20 to 80 mm. The elastic panel 41 may be attached to the leak-barrier sheet 8 at the rear of the transverse center line Q-Q. The elastic panel 41 may also be attached to the leak-barrier sheet 8 so as to extend forward beyond the transverse center line Q-Q unless a dimension by which the panel 41 extends beyond the transverse center line Q-Q exceeds 30 mm. The inner sheet 6 is further provided on the inner surface thereof with the absorbent structure 3 bonded thereto by means of hot melt adhesives (not shown). Of the absorbent panel 33a and the elastic isolating sheet 33b, the absorbent panel 33a has a substantially entire outer surface (i.e., lower surface as viewed in FIG. 4) bonded to the inner sheet 6 so that the absorbent panel 33a cooperates with the inner sheet 6 to sandwich the elastic panel 41. It is also possible to bond the absorbent panel 33a to the elastic panel 41. The elastic isolating sheet 33b is bonded to the inner surface of the absorbent panel 33a along the lateral edges 3a thereof.

Figure 5:
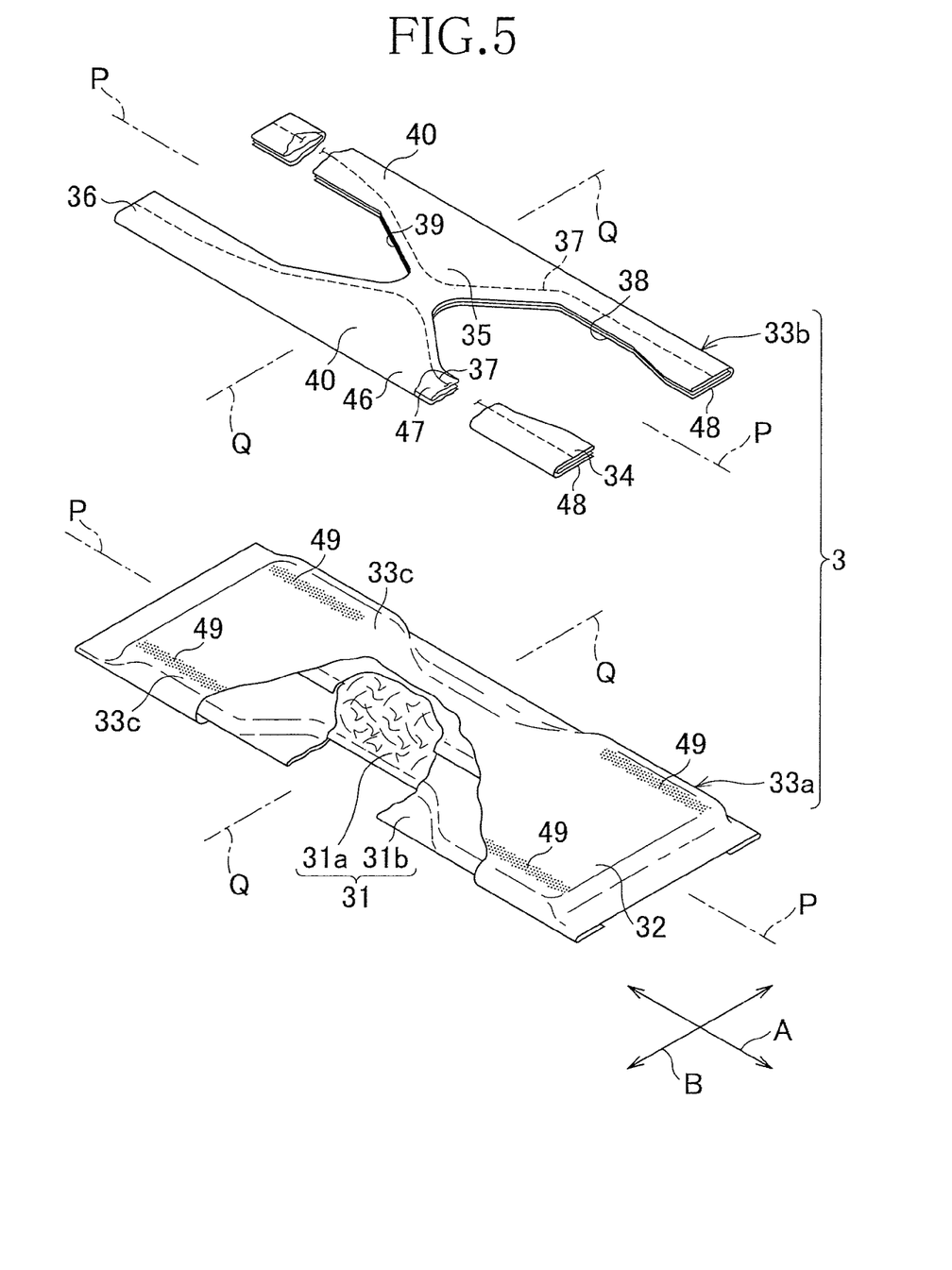
FIG. 5 is an exploded view of a body fluid absorbent assembly.

FIG. 5 is an exploded perspective view of the absorbent structure 3. The absorbent panel 33a constituting the absorbent structure 3 comprises the core 31 formed from liquid-absorbent materials such as fluff pulp fibers, or a mixture of fluff pulp fibers and super-absorbent polymer particles wrapped with a tissue paper, and a liquid-pervious inner sheet 32 at least partially covering the inner surface, the side surfaces and the outer surface of the core 31. FIG. 5 indicates a relationship of this absorbent panel 33a with the longitudinal center line P-P and the transverse center line Q-Q of the diaper 1. The elastic isolating sheet 33b comprises a pair of nonwoven fabric layers 46, 47 put flat together and a pair of crotch elastic members 37 interposed between these nonwoven fabric layers 46, 47 so as to extend symmetrically about the longitudinal center line P-P and bonded in stretched states to at least one of these two nonwoven fabric layers 46, 47. More specifically, the crotch elastic members 37 extend so as to come closest to each other in a width direction B of the elastic isolating sheet 33b, then to extend along peripheries of the front opening 38 and the rear opening 39, and to be gradually spaced apart from each other as these crotch elastic members 37 get nearer to the front end portion 34 and the rear end portion 36, respectively. The lateral portions 34, 36 of the elastic isolating sheet 33b include edges 48 folded back toward the longitudinal center line P-P wherein front and rear end portions 34, 36 of the respective edges 48 are bonded to the inner surface of the absorbent panel 33a along sealing zones 49 provided thereon as indicated by a plurality of dots. Along the front portions 34 and the rear portions 36, the edges 48 folded back and put flat together also are bonded to themselves by means of adhesions or suitable sealing techniques. While the nonwoven fabric layers constituting the elastic isolating sheet 33 may be liquid-pervious or liquid-impervious, it is rather preferable to use nonwoven fabric materials having a liquid-permeability lower than that of the inner sheet 32 in order to ensure that the flow of body fluids from the absorbent panel 33a toward the wearer's skin can be reliably blocked by the elastic isolating sheet 33b even if a central portion 35 of the elastic isolating sheet 33b comes in contact with the absorbent panel 33a in wet condition due to absorption of body fluids during use of the diaper 1.

The diaper 1' of FIG. 3 using such elastic isolating sheet 33b may be folded back on itself along the transverse center line Q-Q and then the front and rear waist regions 12, 13 may be bonded to each other along the lateral edges 15, 16 thereof to obtain the diaper 1 of FIG. 1. Thereupon, the contraction of the crotch elastic members 37 causes at least the intermediate portion 35 of the elastic isolating sheet 33b to be spaced apart upward from the inner sheet 32 of the absorbent panel 33a and to come in contact with the wearer's crotch. It is thus ensured that urine flows toward the absorbent panel 33a through the front opening 38 while feces move toward the absorbent panel 33a through the rear opening 39. In this way, there is no anxiety that wearer's skin between the external genital and the anus might be soiled with bodily waste.

The elastic panel 41 interposed between the covering chassis 2 and the core 31 in the absorbent panel 33a ensures that the absorbent panel 33a can smoothly bow down toward the bottom of the diaper 1 substantially without forming gathers extending in the back-and-forth direction A even when the absorbent panel 33a is compressed in the width direction B as the wearer closes his or her legs. In addition, even if the absorbent panel 33a is compressed together with the elastic panel 41 so as to be folded in two, the absorbent panel 33a can be unfolded under a restorative force of the elastic panel 41 as soon as the wearer opens the legs again. Consequentially, the absorbent panel 33a is substantially free from a potential folding line left thereon. More specifically, the intermediate portion 35 of the elastic isolating sheet 33b is adapted to be kept spaced apart from the absorbent panel 33a by an adequate distance and at the same time the inner surface of the absorbent panel 33a is adapted to extend smoothly, allowing voluminous bodily waste to be received in a space defined between the elastic isolating sheet 33b and the absorbent panel 33a and allowing also a liquid moiety contained in bodily waste to be rapidly absorbed the absorbent panel 33a.

Stock materials for the elastic panel 41 functioning as has been described above may be selected from the group consisting of a foamed elastic sheet having a thickness in a range of 3 to 10 mm and made of foamed resins such as a flexible and elastic foam urethane resin, foam polyethylene resin or foam polystyrene resin; nonwoven fabrics or laminates consisting of plural nonwoven fabric layers having a basis weight in a range of 100 to 250 g/m$^2$ and made of crimped fibers such as mechanically crimped thermoplastic synthetic fibers or thermally crimped thermoplastic synthetic fibers; a nonwoven fabric or laminate consisting of plural nonwoven fabric layers having a basis weight in a range of 100 to 250 g/m$^2$ and containing elastic yarns such as urethane elastic yarns; and a laminate consisting of such foamed elastic sheet and such nonwoven fabric. The foamed elastic sheet preferably has open cells for high air-permeability and, as the crimped fibers, it is preferred to employ composite fibers of sheath-and-core type or side-by-side type and thereby to enhance a restorative force of the elastic panel 41. The elastic panel 41 should have a rate of restoration in the back-and-forth direction A as well as in the width direction B higher than a rate of restoration of non-elastic constituent materials of the diaper in the crotch region 11 inside or outside the elastic panel 41 so that restoration of such sheet materials and core 31 can be promoted by the elastic panel 4 after the diaper 1 has been folded in the back-and-forth direction A and/or the width direction B.

Figure 6:
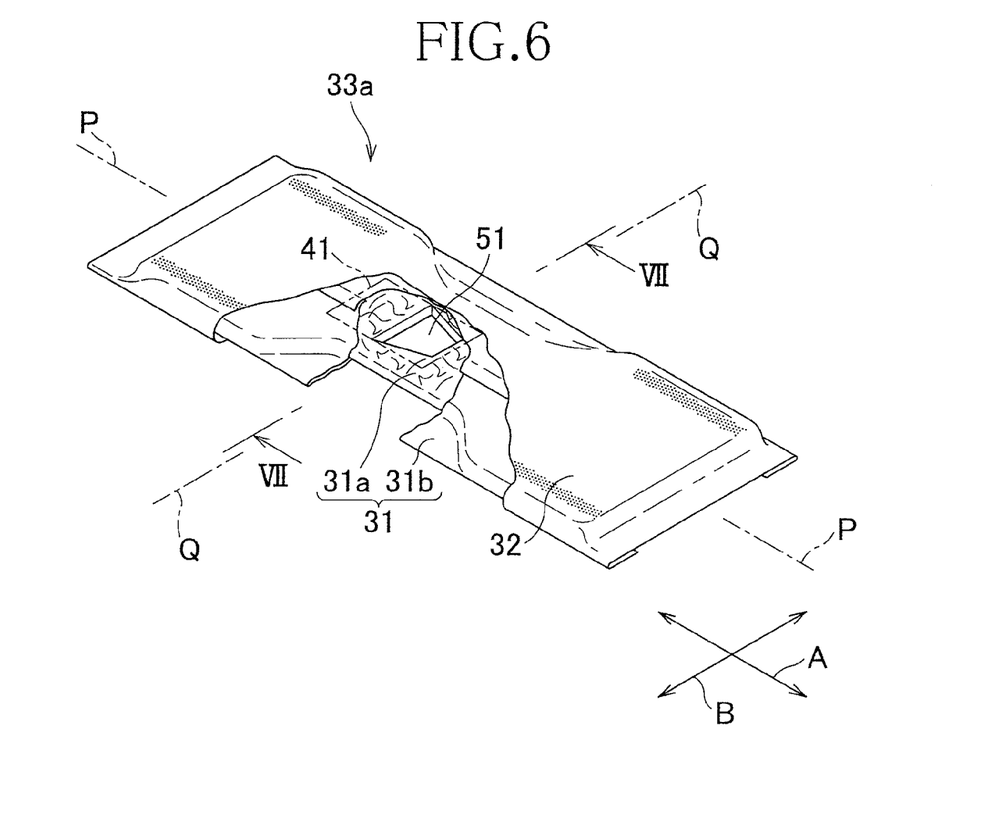
FIG. 6 is a partially cutaway perspective view of a liquid-absorbent panel according to one preferred embodiment of the invention.
Figure 7:
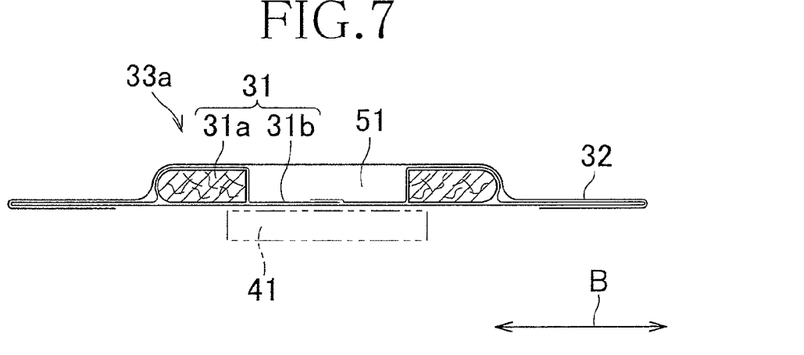
FIG. 7 is a sectional view taken along the line VII-VII in FIG. 6.

FIG. 6 is a partially cutaway perspective view of the liquid-absorbent panel 33a according to one preferred embodiment of the invention and FIG. 7 is a sectional view taken along a line VII-VII in FIG. 6. Referring to FIG. 6, the core 31 of the absorbent panel 33a has no liquid-absorbent material in a vicinity of a point at which the longitudinal center line P-P intersects with the transverse center line Q-Q. In the vicinity of this intersection, instead of the absorbent material, a through-hole 51 extends through the absorbent material 31a in its thickness direction. This absorbent panel 33a also is provided on the outer surface of the core 31 with the elastic panel 41 as indicated by imaginary lines. The absorbent structure 3 including such absorbent panel 33a is substantially free from a possibility that the elastically restorative force of the elastic panel 41 might be diminished by the presence of the core 31. Therefore, even if folded on itself in the width direction B, the absorbent structure 3 according to this embodiment can be quickly unfolded under the effect of the elastic panel 41 more easily than in the case of the absorbent structure 3 of FIG. 5. The formation of the adequately large space between the absorbent panel 33a and the isolating sheet 33b is also ensured more easily than the absorbent panel 33a of FIG. 5. The preferred through-hole 51 has its lower side covered with the tissue paper 31b defining the surface of the absorbent panel 33a. It is also possible to depress the through-hole 51 together with the tissue paper 31b so that the through-hole 51 can be used as a feces receiver. When the diaper 1 is for baby and the through-hole 51 is used for such purpose, the through-hole 51 is preferably put aside forward at a distance of 30 mm or less from the transverse center line Q-Q and a dimension of the through-hole 51 as measured rearward from the transverse center line Q-Q is preferably at least 10 mm longer than a dimension of the through-hole 51 as measured forward from the transverse center line Q-Q and preferably in a range of 30 to 70 mm. While a planar shape of the through-hole 51 is not specified and may be selected from various shapes such as rectangular, square, circular and oval shapes, a shape having a width tapered from its rear end toward its front end such as trapezoidal or a triangular shape is principally preferable. This is because such tapered shape is effective to assure that the absorbent structure 3 is folded along the longitudinal center line P-P alone as a transverse force is exerted on the absorbent structure 3 so as to reduce the width thereof.

Such through-hole 51 as shown may be replaced by a thin and flexible depression containing a smaller amount of the core material 31a than the surrounding portion. The elastic panel 41 underlying the through-hole 51 preferably covers 90% or more and particularly preferable covers 100% of the area of the through-hole 51.

Figure 8:
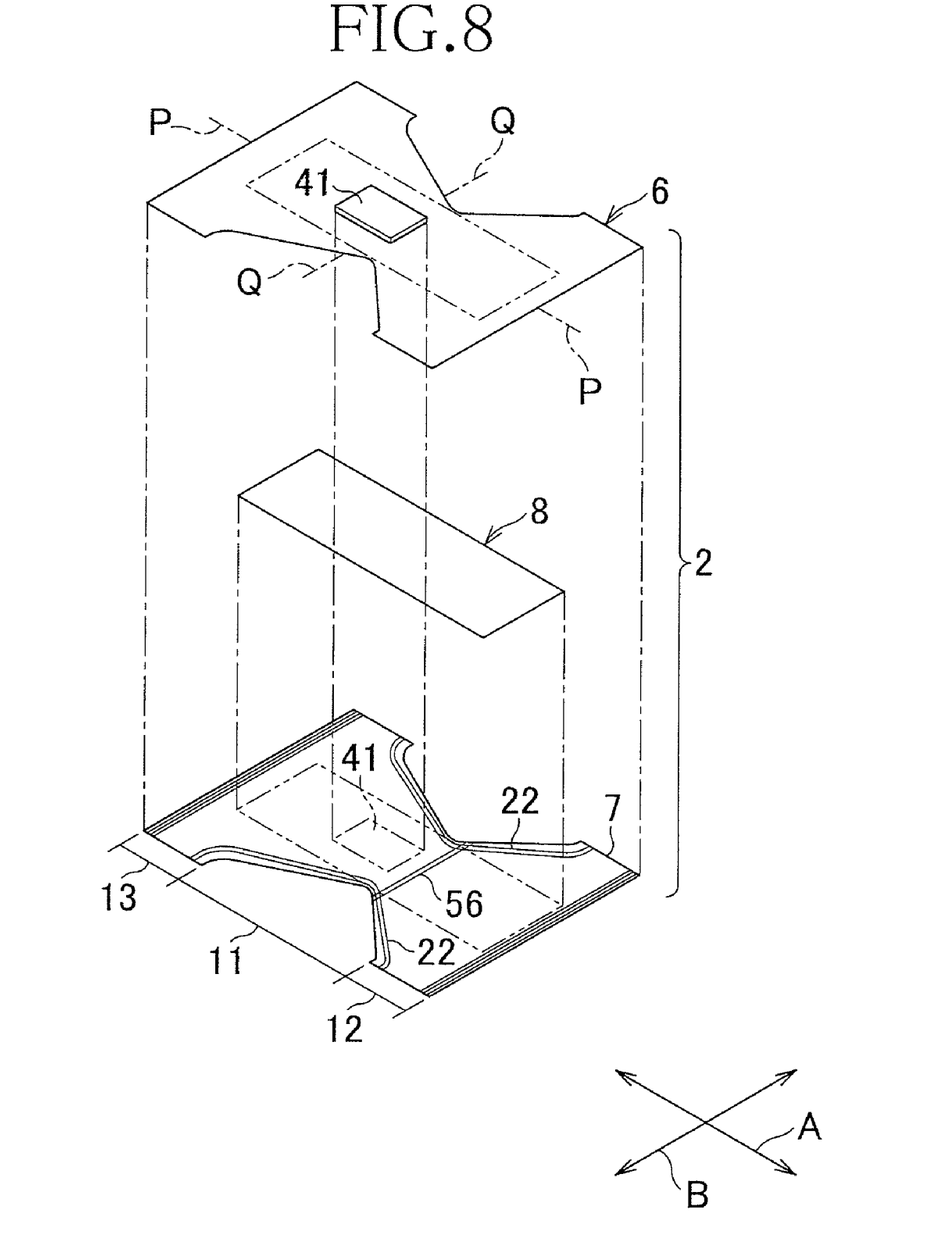
FIG. 8 is an exploded perspective view of a covering chassis according to one preferred embodiment of the invention.

FIG. 8 is an exploded perspective view of the covering chassis 2 which is alternative to the covering chassis 2 of FIG. 4. The covering chassis 2 illustrated herein is provided on the inner surface of the outer sheet 7 in the crotch region 11 with a transverse elastic member 56 extending in the width direction B in the form of elastic string. The transverse elastic member 56 is prepared separately of the leg elastic members 22 and attached in a stretched or non-stretched state to the outer sheet 7 ahead of the elastic panel 41, preferably 5 to 50 mm ahead of the elastic panel 41 so as to extend across the core 31. The transverse elastic member 56 causes the core 31 to be smoothly bowed without the formation of plural gathers extending in the back-and-forth direction A on the core 31 as the wearer closes his or her legs. Consequently, it is possible for the transverse elastic member 56 to prevent an effective area over which the core 31 comes in contact with feces through the intermediary of the inner sheet 32 from being apparently decreased. When such transverse elastic member 56 is attached in a stretched state to the outer sheet 7, a stretching ratio of the elastic member 56 is preferably restrained for possibility that the desired function and effect of the elastic member 56 might be deteriorated.

Figure 9:
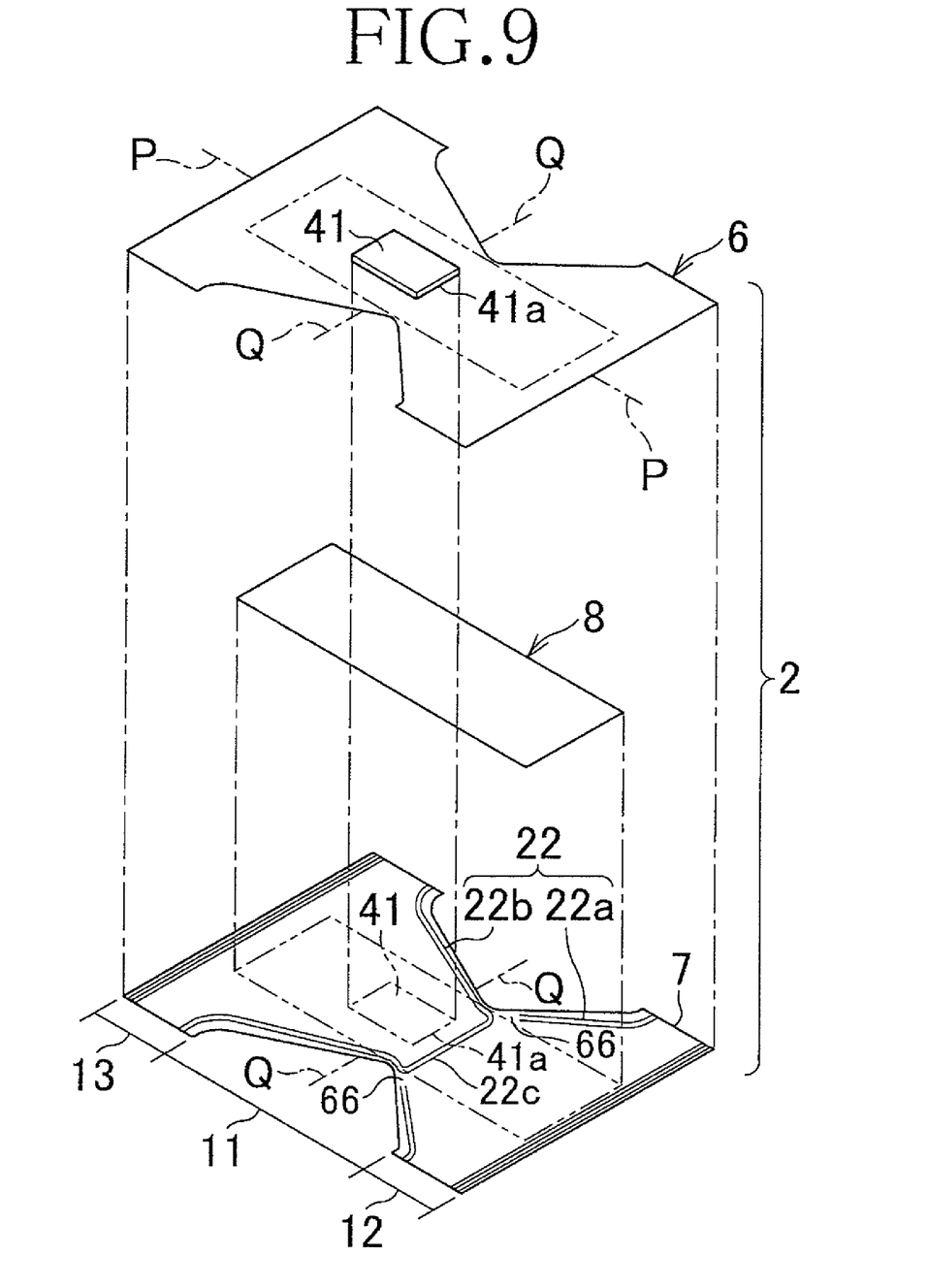
FIG. 9 is a view similar to FIG. 8, showing the covering chassis according to another preferred embodiment of the invention.

FIG. 9 is a view similar to FIG. 8, showing the covering chassis 2 which is alternative to the covering chassis 2 of FIG. 8. In the case of the covering chassis 2 illustrated in FIG. 9, the leg elastic members 22 comprise front elastic members 22a put aside toward the front waist region 12 and rear elastic members 22b put aside toward the rear waist region 13. The front elastic members 22a extend from the front waist region 12 to a vicinity of the transverse center line Q-Q. The rear elastic members 22b extend from the rear waist region 13 beyond a front edge 41a of the elastic panel 41 and then extend across the absorbent structure 3 to define transverse segments 22c. The transverse segments 22c also are attached in a stretched or non-stretched state to the outer sheet 7 and function to prevent the core 31 from being formed with a plurality of gathers.

Figure 10:
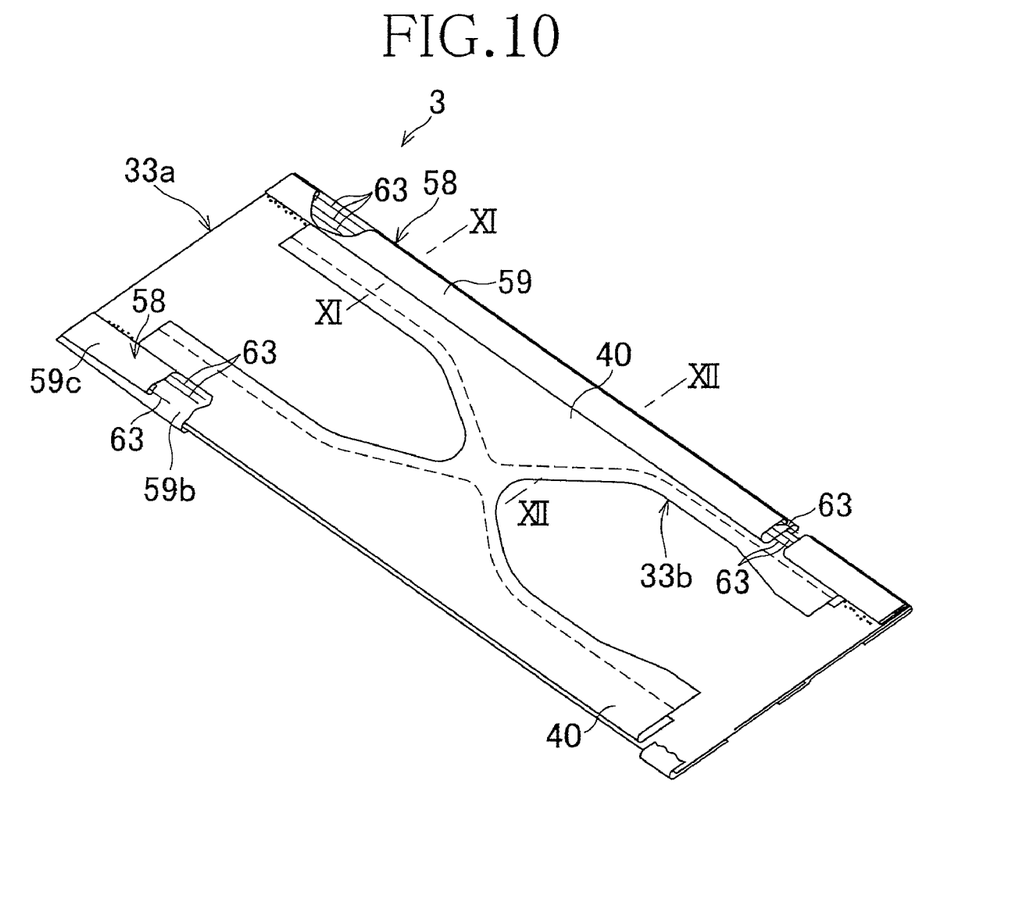
FIG. 10 is a partially cutaway perspective view of the isolating sheet according to one preferred embodiment of the invention.

FIG. 10 is a view similar to FIG. 6 showing of the absorbent structure 3 according to one preferred embodiment of the invention. In the case of the absorbent structure 3 illustrated in FIG. 10, the lateral portions 40 of the isolating sheet 33b are formed on the inner surface with leak-barriers 58. The leak-barriers 58 are formed preferably of a nonwoven fabric, more preferably of a liquid-impervious nonwoven fabric folded back along the lateral portions thereof on themselves in a Z-shape and inverted Z-shape, respectively.

Figure 11:
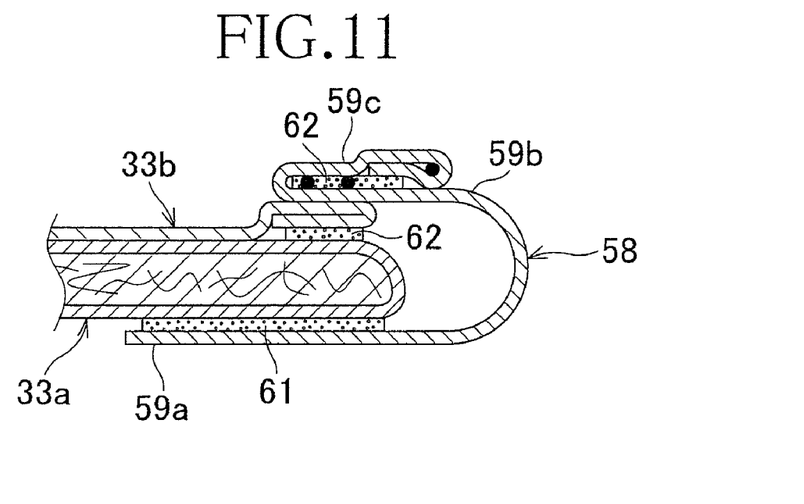
FIG. 11 is a sectional view taken along the line XI-XI in FIG. 10.
Figure 12:
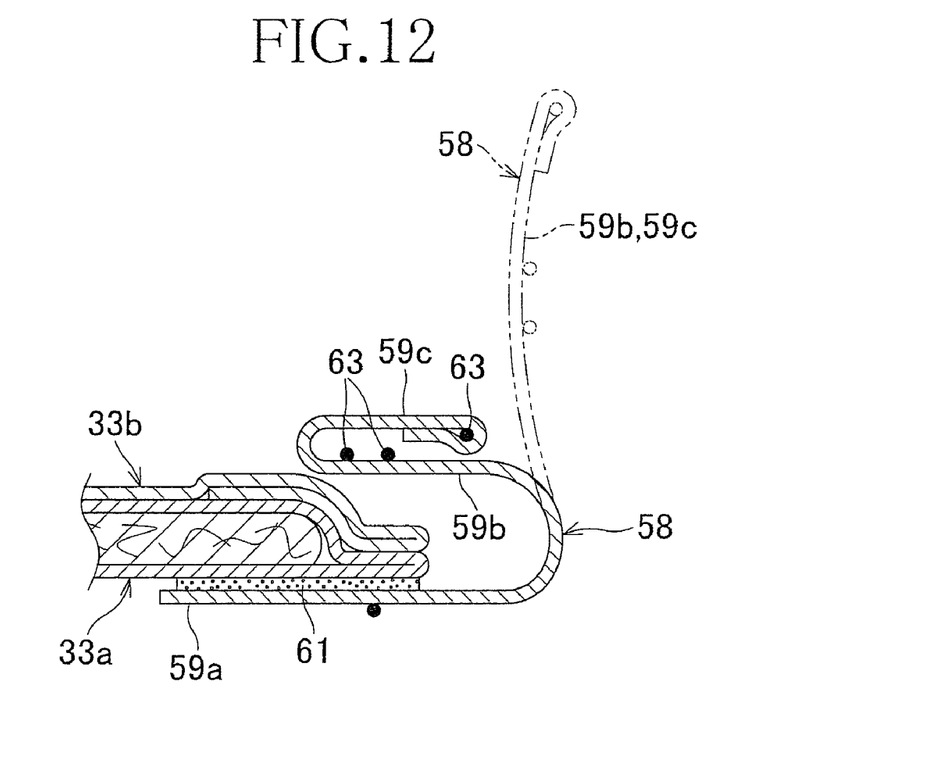
FIG. 12 is a sectional view taken along the line XII-XII in FIG. 10.

FIGS. 11 and 12 are sectional views taken along lines XI-XI and XII-XII in FIG. 10, respectively. The leak-barriers 58 are bonded, with respective bottom sides of the Z- and inverted Z-shapes, to the outer surface of the absorbent panel 33a by means of a hot melt adhesive 61. Respective intermediate sides 59b and top sides 59c of the Z- and inverted Z-shapes are bonded to the inner surface of the absorbent panel 33a or the isolating sheet 33b along longitudinally opposite ends thereof by means of a hot melt adhesive 62. The respective intermediate sides 59b and top sides 59c remain folded back one on another without being bonded together in a vicinity of the transverse center line Q-Q (See FIG. 12). Elastic members 63 are attached in stretched states to the respective intermediate sides 59b and the top sides 59c of the Z- and inverted Z-shapes (See FIG. 10). When the diaper 1 using the absorbent structure including such leak-barriers 58 is configured on the wearer's body as seen in FIG. 1, the intermediate sides 59b as well as the top sides 59c raise themselves up as indicated by imaginary lines in FIG. 12 under contraction of the elastic members 63 in the back-and-forth direction A. In this way, it is unlikely that body fluids might leak sideways from the absorbent structure 3. Such absorbent structure 3 may be used in combination with the covering chassis 2 to achieve a higher protective effect against leak of body fluids through a discontinuous zone defined between the front and rear elastic members 22a, 22b in the crotch region 11 of the covering chassis 2.

Figure 13:
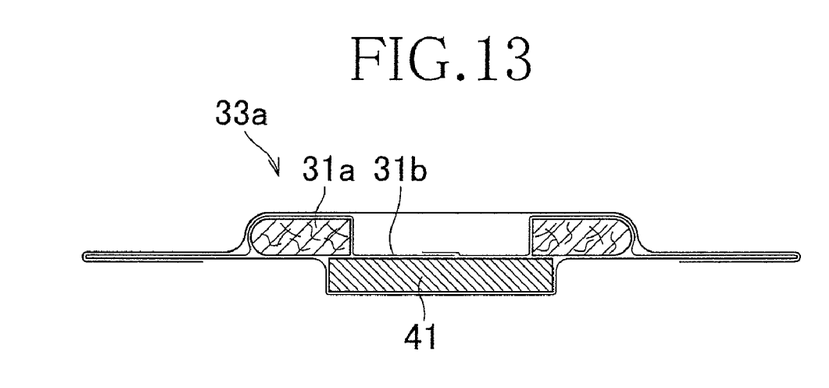
FIG. 13 is a view similar to FIG. 7, showing the liquid-absorbent panel according to another preferred embodiment of the invention.

FIG. 13 is a view similar to FIG. 7, showing the absorbent panel 33a according to another preferred embodiment of the invention. In the case of the absorbent panel 33a exemplarily shown in FIG. 13, the elastic panel 41 is interposed between the outer surface of the absorbent materials' assembly 31a and the tissue paper 31b. The elastic panel 41 according to this embodiment also is provided on the outer surface of the core 31. The elastic panel 41 provided on the outer surface of the core 31 as described herein should be understood to include an elastic panel 41 provided between the inner sheet 6 and the leak-barrier sheet 8, an elastic panel 41 provided between the leak-barrier sheet 8 and the outer sheet 7, and an elastic panel 41 provided on the outer surface of the outer sheet 7, each in the covering chassis 2.

It should be noted that, if needs be, the lateral portions 40 of the elastic isolating sheet 33b may also be bonded to the inner sheet 32 of the absorbent panel 33a, the front and rear openings 38, 39 may be closed in the front and rear waist regions 12, 13, respectively, and although not illustrated, the elastic isolating sheet 33b may be formed so as to entirely cover the inner sheet 6 of the covering chassis 2 wherein at least a peripheral edge of the elastic isolating sheet 33b is bonded to the inner sheet 6. In this embodiment, the elastic isolating sheet 33b may be considered as a constituent element separate of the absorbent structure 3.

What is claimed is:

1. A disposable diaper having a back-and-forth direction and a width direction, said diaper comprising:
   a covering chassis having a front waist region, a rear waist region and a crotch region therebetween;
   an absorbent structure disposed at least in said crotch region;
   an elastic isolating sheet covering at least said absorbent structure and having front and rear end portions and an intermediate portion therebetween, said elastic isolating sheet further including front and rear openings for receiving body waste partitioned by said intermediate portion,
      wherein at least said intermediate portion is adapted to be spaced apart from said absorbent structure under contraction of said elastic isolating sheet, thereby preventing said absorbent structure and a wearer's skin from coming in contact with each other; and
   an elastic panel attached to said absorbent structure in said crotch region and extending in the width direction without extending beyond edges of the absorbent structure, said elastic panel further extending in the back-and-forth direction without extending into the front waist region.

2. The diaper according to claim 1, wherein said elastic panel is adapted to exhibit a higher rate of elastic restoration than that of any non-elastic constituent material of said diaper in said crotch region when said elastic panel bows at least in one of said back-and-forth direction and said width direction.

3. The diaper according to claim 1, wherein said absorbent structure comprises an absorbent panel including a liquid-pervious first sheet,
   a second sheet under said liquid-pervious first sheet, and
   a liquid-absorbent core wrapped by the second sheet.

4. The diaper according to claim 3, wherein said elastic panel has a width corresponding to 20 to 100% of that of said liquid-absorbent core in a bottom lying on a center line of said crotch region in the width direction.

5. The diaper according to claim 3, wherein said liquid-absorbent core is flexible and overlaps said elastic panel.

6. The diaper according to claim 3, further comprising an elastic member which is attached to said liquid-absorbent structure forward of said elastic panel in the back-and-forth direction and extends across said liquid-absorbent core in the width direction.

7. The diaper according to claim 3, wherein said elastic panel is directly attached to said second sheet which wraps the liquid-absorbent core entirely.

8. The diaper according to claim 1, wherein said elastic panel is made of a material selected from the group consisting of foamed polyurethane, foamed polyethylene, foamed polystyrene, crimped thermoplastic synthetic fibers and hollow thermoplastic synthetic fiber.

9. The diaper according to claim 1, wherein said covering chassis comprises one of (i) a plastic film and (ii) a laminate of nonwoven fabrics and a plastic film interposed between said nonwoven fabrics.

10. The diaper according to claim 3, further comprising
    front elastic members extending toward the front waist region; and
    rear elastic members extending from the rear waist region beyond the elastic panel and then extending across the liquid-absorbent core in the width direction for preventing the liquid-absorbent core from being formed with gathers.

11. The diaper according to claim 3, wherein both said elastic panel and the liquid-absorbent core are wrapped by the second sheet.

12. The diaper according to claim 4, wherein said elastic panel is directly attached to said second sheet which wraps the liquid-absorbent core entirely.

13. The diaper according to claim 12, further comprising an elastic member which is attached to said absorbent structure forward of said elastic panel in the back-and-forth direction and extends across said absorbent core in the width direction,
   wherein said elastic member extends across an entire width of the liquid-absorbent core in the width direction in the crotch region for allowing the liquid-absorbent core to smoothly bow without gathers extending in the back-and-forth direction in use.

14. A disposable diaper having a back-and-forth direction and a width direction, said diaper comprising:
   a covering chassis having a front waist region, a rear waist region and a crotch region therebetween;
   an absorbent structure disposed at least in said crotch region;
   an elastic isolating sheet covering at least said absorbent structure and having front and rear end portions and an intermediate portion therebetween, said elastic isolating sheet further including front and rear openings for receiving body waste partitioned by said intermediate portion,
      wherein at least said intermediate portion is adapted to be spaced apart from said absorbent structure under contraction of said elastic isolating sheet, thereby preventing said absorbent structure and a wearer's skin from coming in contact with each other; and an elastic panel attached to said absorbent structure in said crotch region and extending in the width direction without extending beyond edges of the absorbent structure, wherein said absorbent structure comprises an absorbent panel including a liquid-pervious first sheet, a second sheet under said liquid-pervious first sheet, and a liquid-absorbent core wrapped by the second sheet; and wherein said liquid-absorbent core overlaps said elastic panel and includes an opening extending through said liquid-absorbent core in a thickness direction thereof.

15. The diaper according to claim 14, wherein said opening of the liquid-absorbent core overlies the elastic panel in the thickness direction, and the opening is directly covered by said second sheet of the absorbent panel.

16. The diaper according to claim 15, wherein said opening has a trapezoidal shape or a triangular shape.

17. A disposable diaper having a back-and-forth direction and a width direction, said diaper comprising:

a covering chassis having a front waist region, a rear waist region and a crotch region therebetween;

an absorbent structure disposed at least in said crotch region;

an elastic isolating sheet covering at least said absorbent structure and having front and rear end portions and an intermediate portion therebetween, said elastic isolating sheet further including front and rear openings for receiving body waste partitioned by said intermediate portion, wherein at least said intermediate portion is adapted to be spaced apart from said absorbent structure under contraction of said elastic isolating sheet, thereby preventing said absorbent structure and a wearer's skin from coming in contact with each other;

an elastic panel attached to said absorbent structure in said crotch region and extending in the width direction without extending beyond edges of the absorbent structure; and an elastic member attached to said liquid-absorbent structure forward of said elastic panel in the back-and-forth direction and extending across said liquid-absorbent core in the width direction, wherein said absorbent structure comprises an absorbent panel including a liquid-pervious first sheet, a second sheet under said liquid-pervious first sheet, and a liquid-absorbent core wrapped by the second sheet; and wherein said elastic member extends across an entire width of the liquid-absorbent core in the width direction in the crotch region for allowing the liquid-absorbent core to smoothly bow without gathers extending in the back-and-forth direction in use.

* * * * *